(12) United States Patent
Goral

(10) Patent No.: US 8,308,360 B1
(45) Date of Patent: Nov. 13, 2012

(54) DRY POWDER-COATED DENTAL X-RAY FILM AND ASSOCIATED METHOD

(76) Inventor: Irina Goral, East Brunswick, NJ (US)

( * ) Notice: Subject to any disclaimer, the term of this patent is extended or adjusted under 35 U.S.C. 154(b) by 222 days.

(21) Appl. No.: 12/848,139

(22) Filed: Jul. 31, 2010

Related U.S. Application Data

(60) Provisional application No. 61/230,251, filed on Jul. 31, 2009.

(51) Int. Cl.
*A61B 6/14* (2006.01)

(52) U.S. Cl. ........................................ 378/169; 378/210

(58) Field of Classification Search .................. 378/168, 378/169, 191, 210
See application file for complete search history.

(56) References Cited

U.S. PATENT DOCUMENTS

| | | | |
|---|---|---|---|
| 5,327,477 A | 7/1994 | Levy | |
| D415,566 S | 10/1999 | Joyner | |
| 6,382,831 B1 | 5/2002 | Bacchetta et al. | |
| 6,776,525 B1 | 8/2004 | Green | |

*Primary Examiner* — Jurie Yun

(57) ABSTRACT

A dental x-ray film preferably includes a dental x-ray casing adapted to be removably positioned within the patient mouth, an x-ray film contained within the dental x-ray casing, a protective cover removably positioned over the dental x-ray casing such that the dental x-ray casing and the x-ray film are completely contained within the protective cover. Such a protective cover is preferably formed from flexible fluid-impermeable material. A dry powder is preferably coated on a major surface area of an outer surface of at least one of the protective cover and the dental x-ray casing. Notably, the dry powder is fluid-soluble and includes an anesthetic agent and/or a flavoring agent capable of providing a numbing effect and a desirable taste when exposed to fluid, respectively, during the dental x-ray procedure.

11 Claims, 5 Drawing Sheets

DRY POWDER-COATED DENTAL X-RAY FILM AND ASSOCIATED METHOD

CROSS REFERENCE TO RELATED APPLICATIONS

This application claims the benefit of U.S. Provisional Application No. 61/230,251, filed Jul. 31, 2009, the entire disclosures of which are incorporated herein by reference.

STATEMENT REGARDING FEDERALLY SPONSORED RESEARCH OR DEVELOPMENT

Not Applicable.

REFERENCE TO A MICROFICHE APPENDIX

Not Applicable.

BACKGROUND OF THE INVENTION

1. Technical Field

This invention relates to dental x-ray films and, more particularly, to a dry powder-coated dental x-ray film having flavored and/or anesthetic properties and thereby providing a user with relaxed and enjoyable dental x-ray experience.

2. Prior Art

To have a healthy smile, the American Dental Association recommends that consumers visit a dentist office at least twice a year for a routine cleaning. A trip to the dentist office also often involves having X-rays taken of the teeth and gums. X-rays are pictures of the teeth, bones, and soft tissues which are utilized to find problems with the teeth, mouth, and jaw. X-ray pictures can show cavities, hidden dental structures (such as wisdom teeth), and bone loss that cannot be seen during a visual examination. Dental X-rays may also be done as follow-up after dental treatments. Bitewing X-rays are used to check for decay between the teeth and to show how well the upper and lower teeth line up. They also show bone loss when severe gum disease or a dental infection is present. There are five types of X-rays commonly utilized by dentists: bitewing, periapical, occlusal, and panoramic.

Regardless of what type of X-ray a dentist may choose to utilize, having X-rays performed can be extremely uncomfortable for the patient. During an X-ray, the dentist or dental X-ray technician will have the patient bite down on a small piece of cardboard or plastic which holds the actual X-ray film. Some people may gag on the original bitter taste of plastic or cardboard with XCP holder that holds the X-ray film. This is especially prevalent with young children who often find biting down on X-ray film to be a miserable and uncomfortable experience.

Accordingly, a need remains for an apparatus in order to overcome the above-noted shortcomings. The present invention satisfies such a need by providing a powder-coated dental x-ray film having anesthetic and/or flavored properties that is convenient and easy to use, is durable yet lightweight in design, is versatile in its applications, and provides a user with a more relaxed and enjoyable dental x-ray experience.

BRIEF SUMMARY OF THE INVENTION

In view of the foregoing background, it is therefore an object of the present invention to provide a powder-coated dental x-ray film having flavored and/or anesthetic properties and thereby providing a user with relaxed and enjoyable dental x-ray experience. In one embodiment, a clear polyethylene plastic may be provided with a coating of flavored dry powder, for example. Such a dry powder may provide various tastes such as berries and menthol, for example. This helps prevent the psychological and gag reflex and produces a pleasant feeling for the when taking x-rays. This is especially helpful for taking children's x-rays. If the patient has abscessing or anatomical anomalies (such as a small jaw or muscles), conventional x-ray films often create sharp pain. The present invention overcomes this problem by providing an anesthetic agent to the dry powder, which partially removes some of the pain and discomfort in the period of taking periapical or bitewing x-rays. In one embodiment, the dry powder may not include sugar, so for patients with diabetes or for whose watching their weight, product is not harmful. Of course, the powder is also non-toxic and may be calorie free.

In one embodiment, for digital x-rays, the powder coating does not have any additional side effects. For non-digital x-rays, it does not leave a radioplaque effect or white spots on the x-ray film In one embodiment, the first few minutes after the x-ray technician places the film into the mouth, taste receptors and saliva are focused on the taste of the film so the patient does not think about their discomfort and is distracted from pain. This gives the technician additional time for set up and exposure of the x-ray. The variety of flavors for the coating creates a good relationship between the patient and dental personnel.

In one embodiment, flavored protective covers may be used for intra-oral cameras and dual-light cures.

These and other objects, features, and advantages of the invention are provided by a dental x-ray film for reducing discomfort inside a patient mouth during a dental x-ray procedure. Such a dental x-ray film preferably includes a dental x-ray casing adapted to be removably positioned within the patient mouth, an x-ray film contained within the dental x-ray casing, a protective cover removably positioned over the dental x-ray casing such that the dental x-ray casing and the x-ray film are completely contained within the protective cover. Such a protective cover is preferably formed from flexible fluid-impermeable material. A dry powder is preferably coated on a major surface area of an outer surface of at least one of the protective cover and the dental x-ray casing. Notably, the dry powder is fluid-soluble and includes an anesthetic agent capable of providing a numbing effect when exposed to fluid during the dental x-ray procedure.

In one embodiment, the fluid-impermeable material may include polyethylene and is transparent such that the x-ray film is capable of being viewed from an exterior of the protective cover.

In one embodiment, the dry powder may further include a flavored agent capable of providing a pleasant taste when exposed to fluid during the dental x-ray procedure.

In one embodiment, the anesthetic and flavored agents are preferably located at mutually exclusive regions of the dental x-ray casing.

In one embodiment, the anesthetic and flavored agents may be mixed together.

The present invention may further include a method of utilizing a dental x-ray film for reducing discomfort inside a patient mouth during a dental x-ray procedure. Such a method preferably includes the chronological steps of: providing a dental x-ray casing; providing and containing an x-ray film within the dental x-ray casing; providing a protective cover formed from flexible fluid-impermeable material; providing and coating a dry powder on a major surface area of an outer surface of at least one of the protective cover and the dental x-ray casing, wherein the dry powder being fluid-soluble and including an anesthetic agent.

The method further includes the chronological steps of: removably positioning the protective cover over the dental x-ray casing such that the dental x-ray casing and the x-ray film are completely contained within the protective cover; during a dental x-ray procedure, removably positioning the dental x-ray casing and the protective cover within the patient mouth; and providing a numbing effect to an intraoral cavity of the patient mouth by exposing the dry powder to fluid during the dental x-ray procedure.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

It is noted the purpose of the foregoing abstract is to enable the U.S. Patent and Trademark Office and the public generally, especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE SEVERAL VIEWS OF THE DRAWING

The novel features believed to be characteristic of this invention are set forth with particularity in the appended claims. The invention itself, however, both as to its organization and method of operation, together with further objects and advantages thereof, may best be understood by reference to the following description taken in connection with the accompanying drawings in which:

Figure 1:
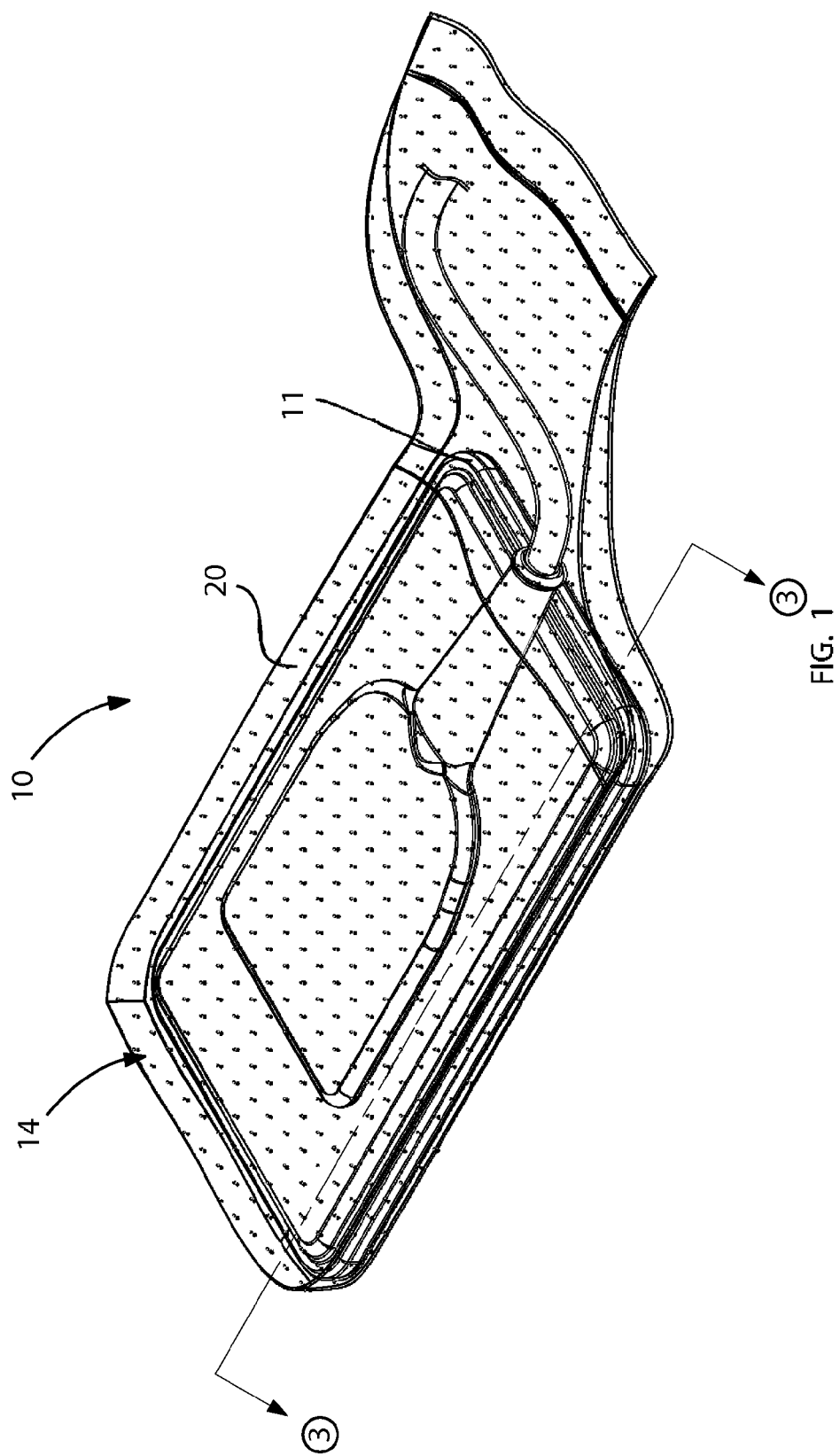
FIG. 1 is a perspective view showing a dental x-ray casing provided with a protective cover coated with dry powder having anesthetic and flavored agents, in accordance with the present invention.

Those skilled in the art will appreciate that the figures are not intended to be drawn to any particular scale; nor are the figures intended to illustrate every embodiment of the invention. The invention is not limited to the exemplary embodiments depicted in the figures or the shapes, relative sizes or proportions shown in the figures.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiment set forth herein. Rather, this embodiment is provided so that this application will be thorough and complete, and will fully convey the true scope of the invention to those skilled in the art. Like numbers refer to like elements throughout the figures.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "present invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. §1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The below disclosed subject matter is to be considered illustrative, and not restrictive, and the appended claims are intended to cover all such modifications, enhancements, and other embodiments which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

The apparatus of this invention is referred to generally in FIGS. 1-5 by reference numeral 10 and is intended to provide a dental x-ray film apparatus 10 for reducing discomfort inside a patient's mouth during a dental x-ray procedure. It should be understood that dental x-ray film apparatus 10 may be produced in a variety of forms such as bitewing, periapical, occlusal, and panoramic casings, for example.

Such a dental x-ray film apparatus 10 preferably includes a dental x-ray casing 11 adapted to be removably positioned within the patient's mouth, an x-ray film 12 contained within the dental x-ray casing 11, a protective cover 20 removably positioned over the dental x-ray casing 11 such that the dental x-ray casing 11 and the x-ray film 12 are completely contained within the protective cover 20. Such a protective cover 20 is preferably formed from flexible fluid-impermeable material 15 such as clear plastic, for example.

In one embodiment, the fluid-impermeable material 15 may include polyethylene and is transparent such that the dental x-ray casing 11 is capable of being viewed from an exterior of the protective cover 20.

Advantageously, a dry powder 14 is coated on a major surface area of an outer surface of at least one of the protective cover 20 and the dental x-ray casing 11. Notably, the dry powder 14 is fluid-soluble and includes an anesthetic agent 17 capable of providing a numbing effect when exposed to fluid during the dental x-ray procedure.

The dry powder 14 may coat the plastic protective cover 20 or dental x-ray casing 11, as opposed to the x-ray film 12 itself. The dry powder 14 can be any conventional dry powder 14 used for food preparations, for example. Any number of fruit flavors, such as cinnamon and mint could be offered. For example, the dry powder 14 may include be any conventional flavor such as lemon, mint, cherry, strawberry, bubble gum, pina-colada or other such flavors. The flavor chosen may depend on the person for whom it is meant, such as bubble gum for a child. Additionally, it is desirable to offer the dental x-ray casing 11 and/or the protective cover 20 in a plurality of sizes for the accommodation of different sized mouths.

Experiencing delicious flavors as the dental x-ray casing 11 and/or the protective cover 20 is inserted into the mouth, the patient would be more likely to relax and hold the dental x-ray casing 11 and/or the protective cover 20 in their mouth, as opposed to gagging and spitting it out.

One skilled in the art understands a variety of well-known techniques may be employed for coating the dry powder 14 onto the dental x-ray casing 11 and/or protective cover 20. For example, the dry powder 14 may be brushed, sprayed, sprinkling or rolled onto the outer surface of the dental x-ray casing 11 and/or the protective cover 20. Such techniques may be preferred where it is desired to apply the dry powder 14 only to selected regions of the dental x-ray casing 11 and/or the protective cover 20. This may be done during the process of manufacturing the dental x-ray casing 11 and/or the protective cover 20 or after they have been made. This approach could even be applied in the dentist's office on an as needed basis, for example.

In one embodiment, the dry powder 14 may further include a flavored agent 16 capable of providing a pleasant taste when exposed to fluid during the dental x-ray procedure.

In one embodiment, the anesthetic agent 17 may be mixed with the flavoring agent 16, thus providing patients who are suffering cavities or an abscess a more comfortable means of having a dental x-ray taken.

Figure 5:
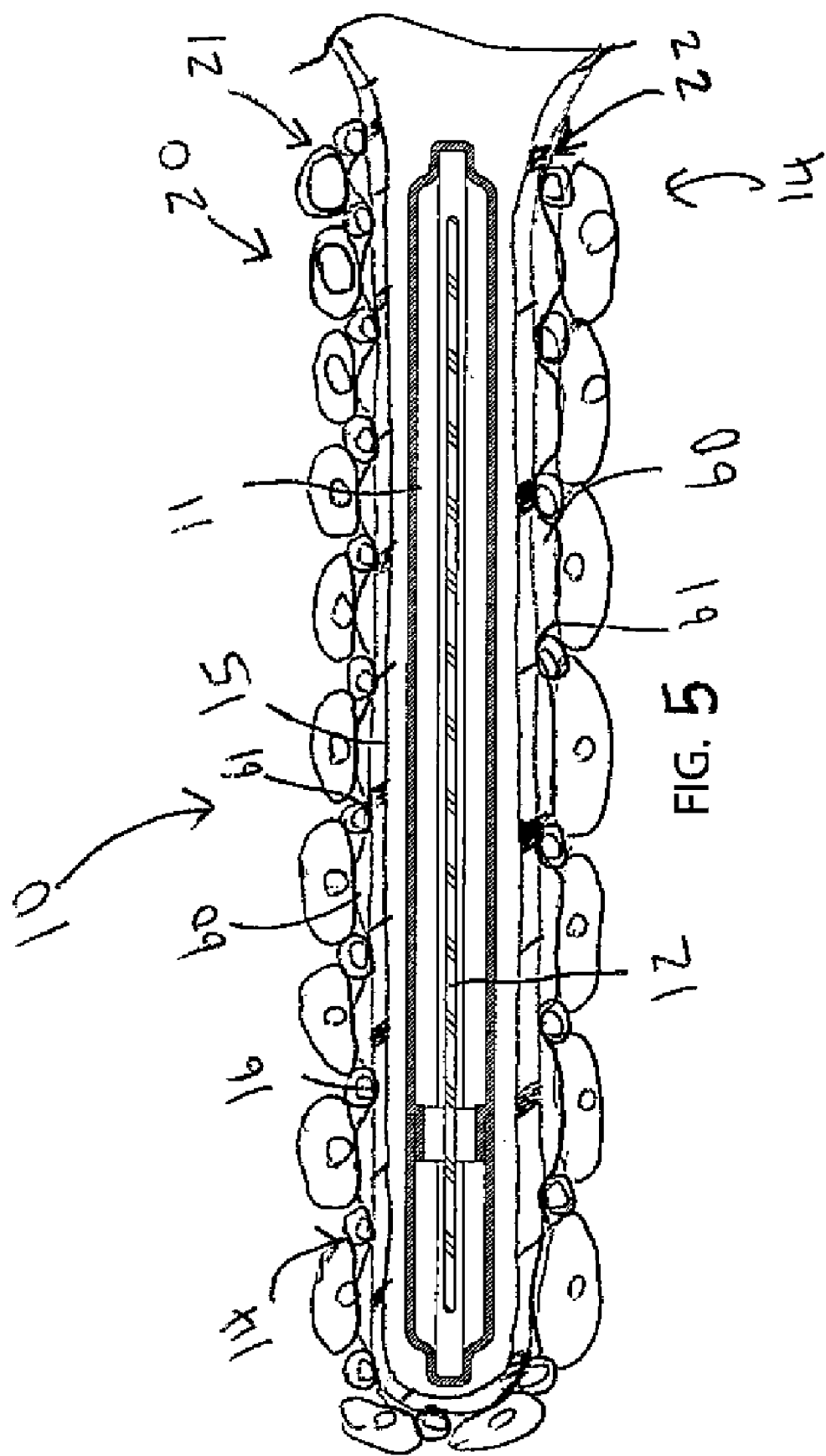
FIG. 5 is a cross-sectional view showing first and second layers of dry powder located on crests and troughs formed along the outer surface of the protective cover.

In one embodiment, as perhaps best shown in FIG. 5, a first layer 21 of dry powder 14 may be applied as a separate layer, distinct from a second layer 22 of dry powder 14. In this embodiment, the first layer 21 contains the anesthetic agent 17 and the second layer 22 contains the flavoring agent 16. This is especially applicable where the dental x-ray casing 11 and/or the protective cover 20 is made of vinyl or a similar material 15 which does not absorb significant amounts of dry powder 14. In such scenarios, as a non-limiting example, the outer surfaces of the dental x-ray casing 11 and/or the protective cover 20 may be etched to create crests 60 and troughs 61 for receiving and containing the separate layers 21, 22 of dry powder 14.

In particular, the first layer 21 of dry powder 14 sits on the crests 60 and the second layer 22 of dry powder 14 sits in the troughs 61. While FIG. 5 shows the first layer 21 dry powder 14 having a size than the second layer 22 dry powder 14, such sizes are not drawn to scale and are not intended to have any limiting effect on the relative sizes of dry powder 14 on each layer 21, 22. The same reasoning is applied to the crests 60 and troughs 61. Advantageously, the dry powder 14 does not transform into a gel or liquid state until saliva from the patient's mouth contacts the dry powder 14. Such a feature provides the benefit of extending a shelf-life of the anesthetic 17 flavoring 16 agents that are contained within the dry powder 14.

Figure 3:
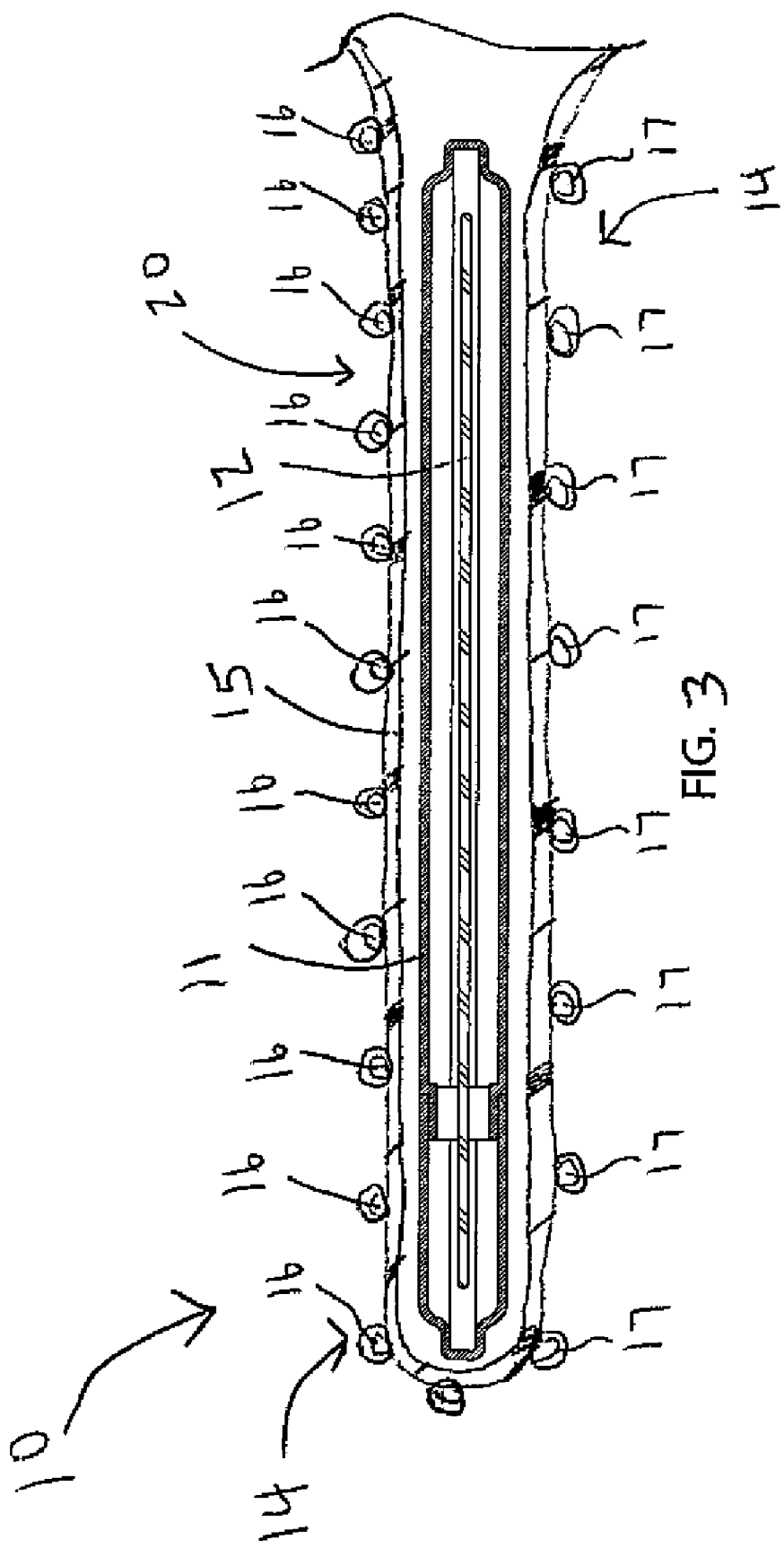
FIG. 3 is a perspective view showing a dental x-ray casing provided with a protective cover coated with dry powder having anesthetic and flavored agents, in accordance with the present invention.

In one embodiment, the anesthetic 17 and flavored 16 agents are preferably located at mutually exclusive regions of the protective cover 20, as perhaps best shown in FIGS. 1 and 3.

Figure 2:
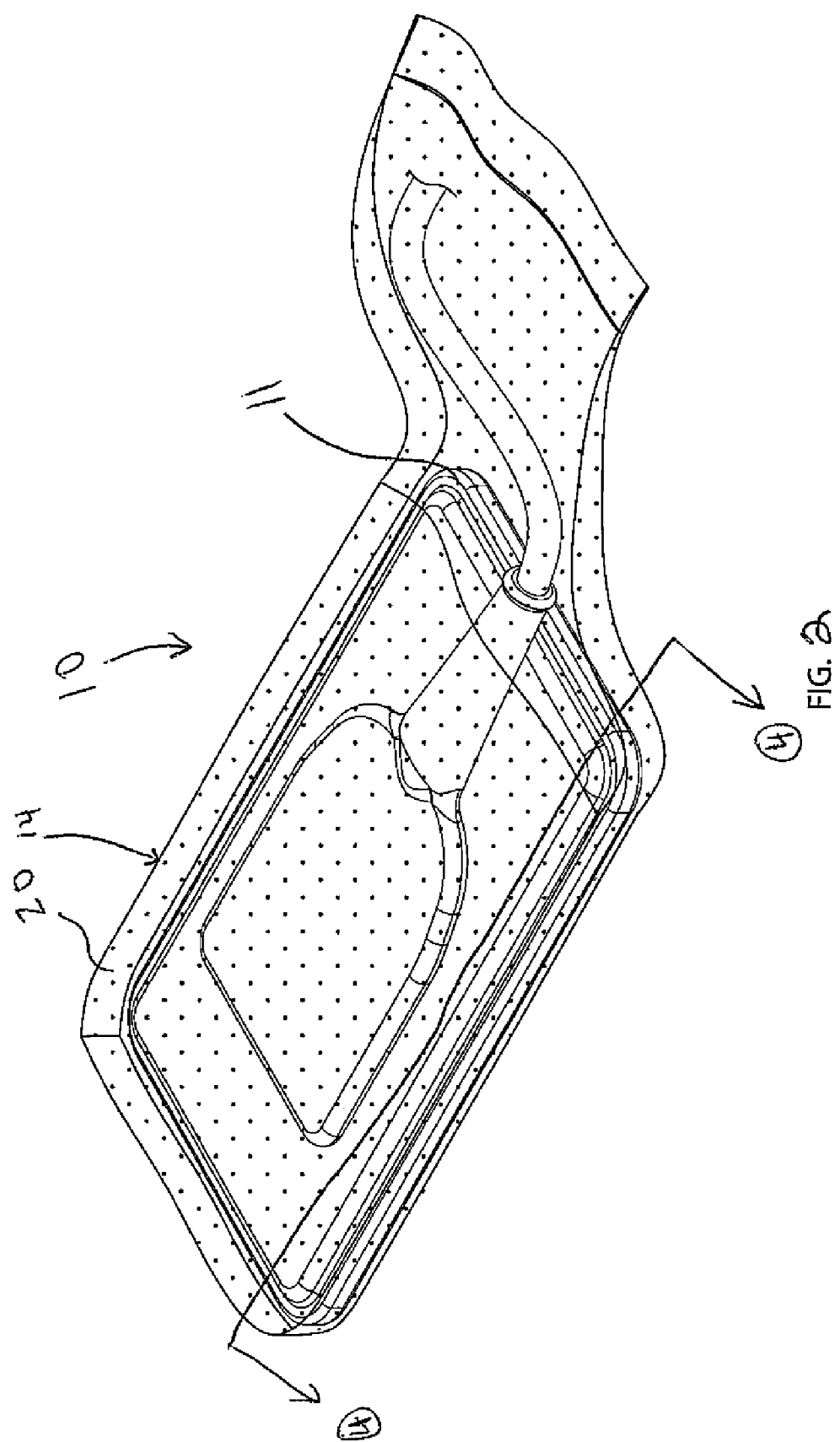
FIG. 2 is a cross-sectional view taken along line 2-2 in FIG. 1 showing the anesthetic and flavored agents dispersed along overlapping regions of a major surface area of the protective cover.
Figure 4:
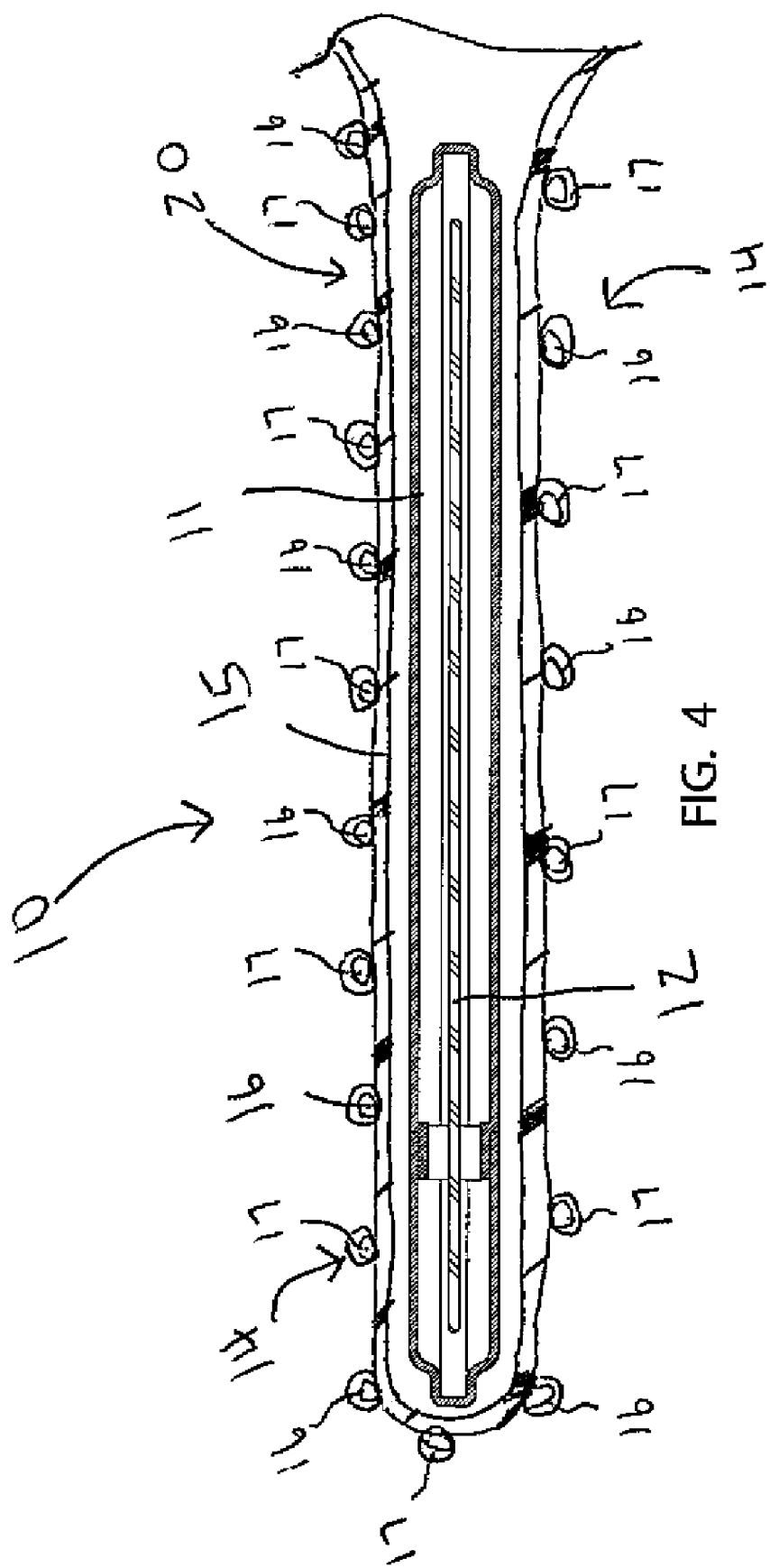
FIG. 4 is a cross-sectional view taken along line 4-4 in FIG. 3 showing the anesthetic and flavored agents dispersed along mutually exclusive regions of a major surface area of the protective cover.

In one embodiment, the anesthetic 17 and flavored 16 agents may be mixed together, as perhaps best shown in FIGS. 2 and 4.

The present invention may further include a method of utilizing a dental x-ray film apparatus 10 for reducing discomfort inside a patient's mouth during a dental x-ray procedure. Such a method preferably includes the chronological steps of: providing a dental x-ray casing 11; providing and containing an x-ray film 12 within the dental x-ray casing 11; providing a protective cover 20 formed from flexible fluid-impermeable material 15; providing and coating a dry powder 14 on a major surface area of an outer surface of at least one of the protective cover 20 and the dental x-ray casing 11, wherein the dry powder 14 is fluid-soluble and includes an anesthetic agent 17.

The method further includes the chronological steps of: removably positioning the protective cover 20 over the dental x-ray casing 11 such that the dental x-ray casing 11 and the x-ray film 12 are completely contained within the protective cover 20; during a dental x-ray procedure, removably positioning the dental x-ray casing 11 and the protective cover 20 within the patient's mouth; and providing a numbing effect to an intraoral cavity of the patient mouth by exposing the dry powder 14 to fluid, such as saliva, during the dental x-ray procedure.

While the invention has been described with respect to a certain specific embodiment, it will be appreciated that many modifications and changes may be made by those skilled in the art without departing from the spirit of the invention. It is intended, therefore, by the appended claims to cover all such modifications and changes as fall within the true spirit and scope of the invention. In particular, with respect to the above description, it is to be realized that the optimum dimensional relationships for the parts of the present invention may include variations in size, materials, shape, form, technology, function and manner of operation.

What is claimed as new and what is desired to secure by Letters Patent of the United States is:

1. A dental x-ray film apparatus for reducing discomfort inside a patient mouth during a dental x-ray procedure, said dental x-ray film apparatus comprising:
   a dental x-ray casing adapted to be removably positioned within the patient mouth;
   an x-ray film contained within said dental x-ray casing;

a protective cover removably positioned over said dental x-ray casing such that said dental x-ray casing and said x-ray film are completely contained within said protective cover; and a dry powder coated on a major surface area of an outer surface of at least one of said protective cover and said dental x-ray casing;

wherein said dry powder is fluid-soluble and comprises an anesthetic agent capable of providing a numbing effect when exposed to fluid during the dental x-ray procedure.

2. The dental x-ray film apparatus of claim 1, wherein said protective cover is formed from flexible polyethylene and is transparent such that said x-ray casing is capable of being viewed from an exterior of said protective cover.

3. The dental x-ray film apparatus of claim 1, wherein said dry powder further comprises: a flavored agent capable of providing a pleasant taste when exposed to fluid during the dental x-ray procedure.

4. The dental x-ray film apparatus of claim 3, wherein said anesthetic and flavored agents are located at mutually exclusive regions of said dental x-ray casing.

5. The dental x-ray film apparatus of claim 3, wherein said anesthetic and flavored agents are mixed together.

6. A dental x-ray film apparatus for reducing discomfort inside a patient mouth during a dental x-ray procedure, said dental x-ray film apparatus comprising:

a dental x-ray casing adapted to be removably positioned within the patient mouth;

an x-ray film contained within said dental x-ray casing;

a protective cover removably positioned over said dental x-ray casing such that said dental x-ray casing and said x-ray film are completely contained within said protective cover; and a dry powder coated on a major surface area of an outer surface of at least one of said protective cover and said dental x-ray casing;

wherein said dry powder is fluid-soluble and comprises an anesthetic agent capable of providing a numbing effect when exposed to fluid during the dental x-ray procedure;

wherein said protective cover is formed from flexible fluid-impermeable material.

7. The dental x-ray film apparatus of claim 6, wherein said fluid-impermeable material comprises: polyethylene and is transparent such that said x-ray casing is capable of being viewed from an exterior of said protective cover.

8. The dental x-ray film apparatus of claim 6, wherein said dry powder further comprises: a flavored agent capable of providing a pleasant taste when exposed to fluid during the dental x-ray procedure.

9. The dental x-ray film apparatus of claim 8, wherein said anesthetic and flavored agents are located at mutually exclusive regions of said dental x-ray casing.

10. The dental x-ray film apparatus of claim 8, wherein said anesthetic and flavored agents are mixed together.

11. A method of utilizing a dental x-ray film apparatus for reducing discomfort inside a patient mouth during a dental x-ray procedure, said method comprising the chronological steps of:

providing a dental x-ray casing;

providing and containing an x-ray film within said dental x-ray casing;

providing a protective cover formed from flexible fluid-impermeable material;

providing and coating a dry powder on a major surface area of an outer surface of at least one of said protective cover and said dental x-ray casing, said dry powder being fluid-soluble and comprising an anesthetic agent;

removably positioning said protective cover over said dental x-ray casing such that said dental x-ray casing and said x-ray film are completely contained within said protective cover;

during a dental x-ray procedure, removably positioning said dental x-ray casing and said protective cover within the patient mouth; and providing a numbing effect to an intraoral cavity of the patient mouth by exposing said dry powder to fluid during the dental x-ray procedure.

* * * * *